US009566597B2

(12) United States Patent
McKay (10) Patent No.: US 9,566,597 B2
(45) Date of Patent: *Feb. 14, 2017

(54) ON-BOARD WATER SPRAY SYSTEM FOR AIRCRAFT

(71) Applicant: Textron Innovations, Inc., Providence, RI (US)

(72) Inventor: Gary E. McKay, Wichita, KS (US)

(73) Assignee: Textron Innovations, Inc., Providence, RI (US)

( * ) Notice: Subject to any disclaimer, the term of this patent is extended or adjusted under 35 U.S.C. 154(b) by 106 days.

This patent is subject to a terminal disclaimer.

(21) Appl. No.: 14/270,301

(22) Filed: May 5, 2014

(65) Prior Publication Data

US 2014/0239085 A1    Aug. 28, 2014

Related U.S. Application Data

(63) Continuation of application No. 12/760,939, filed on Apr. 15, 2010, now Pat. No. 8,713,987.

(51) Int. Cl.
*B64D 47/00* (2006.01)
*B05B 12/12* (2006.01)
(Continued)

(52) U.S. Cl.
CPC .............. *B05B 12/126* (2013.01); *B60T 8/56* (2013.01); *B60T 17/221* (2013.01); *B64C 25/32* (2013.01);
(Continued)

(58) Field of Classification Search
CPC ...... B60T 8/56; B60T 17/221; B60T 2210/12; B60T 2210/13; B60T 2270/406; B64C 25/32; B64D 1/18; G01N 19/02; B05B 12/126; B05B 9/06; B05B 12/12; B64F 5/0045; G01M 1/122; G01M 1/125; G01M 1/127; G06G 7/70; B60P 3/30; Y10T 137/6906
(Continued)

(56) References Cited

U.S. PATENT DOCUMENTS 2,466,150 A    1/1944  Burt
2,664,256 A   12/1953  Winterringer
(Continued)

FOREIGN PATENT DOCUMENTS

DE    2701695    4/1985
GB    2462528    2/2010

OTHER PUBLICATIONS

Federal Aviation Administration, Advisory Circular on the subject of Measurement, Construction, and Maintenance of Skid-Resistant Airport Pavement Surfaces, Mar. 18, 1997.*
(Continued)

*Primary Examiner* — Michael A Lyons
*Assistant Examiner* — David L Singer
(74) *Attorney, Agent, or Firm* — Erise IP, P.A.

(57) ABSTRACT

A system for simulating wet runway conditions by using a liquid container that is placed inside an aircraft. The liquid container is connected to a nozzle that sprays water in front of the wheels of the aircraft. A valve is used to control the flow of water from the nozzle. Systems, such as the braking system of the aircraft, can then be tested in wet runway conditions simulated by the system. The amount of water sprayed from the nozzle can also be electronically controlled in relation to the speed of the aircraft, such that the nozzle sprays a nearly uniform layer of liquid in front of the wheels. The system can also be modified to include two tanks to manipulate the center of gravity of the aircraft.

15 Claims, 5 Drawing Sheets

(51) Int. Cl.
*B60T 8/56* (2006.01)
*B60T 17/22* (2006.01)
*B64C 25/32* (2006.01)
*B64D 1/18* (2006.01)
*B64F 5/00* (2006.01)
*G01N 19/02* (2006.01)

(52) U.S. Cl.
CPC .............. *B64D 1/18* (2013.01); *B64F 5/0045* (2013.01); *G01N 19/02* (2013.01); *B60T 2210/12* (2013.01); *B60T 2210/13* (2013.01); *B60T 2270/406* (2013.01); *Y10T 137/6906* (2015.04)

(58) Field of Classification Search
USPC ....... 73/9; 137/899.2; 239/171, 11; 701/124; 702/169
See application file for complete search history.

(56) References Cited

U.S. PATENT DOCUMENTS

| | | | | |
|---|---|---|---|---|
| 2,672,880 A * | 3/1954 | Hermanson | ........... | G01F 23/266 114/121 |
| 2,677,516 A * | 5/1954 | Pilling | .................... | B64C 25/32 239/171 |
| 2,841,164 A * | 7/1958 | Williamson | ........... | B64D 37/20 137/98 |
| 2,926,688 A * | 3/1960 | Muma | .................... | B64D 37/20 137/263 |
| 2,948,146 A * | 8/1960 | Bergeson | .............. | G01M 1/127 73/65.06 |
| 3,182,934 A * | 5/1965 | Clark | .................... | B60B 39/026 244/103 R |
| 3,266,728 A * | 8/1966 | Hallberg | ............. | A01M 7/0089 137/491 |
| 3,339,865 A * | 9/1967 | Nettles | .................... | B64C 25/32 244/103 R |
| 3,645,313 A | 2/1972 | Roberts et al. | | |
| 3,680,885 A * | 8/1972 | DeCardi | ................. | B60B 39/00 244/103 R |
| 3,782,634 A * | 1/1974 | Herman | .............. | A01M 7/0089 222/627 |
| 3,877,645 A * | 4/1975 | Oligschlaeger | ..... | A01M 7/0089 239/155 |
| 4,052,003 A * | 10/1977 | Steffen | ................ | A01M 7/0089 239/155 |
| 4,099,688 A * | 7/1978 | Jayne | ..................... | B64C 25/32 137/74 |
| 4,175,701 A * | 11/1979 | Wojciechowski | .... | F04D 15/0218 239/11 |
| 4,193,547 A * | 3/1980 | Ballu | ....................... | B05B 9/06 222/614 |
| 4,220,998 A * | 9/1980 | Kays | ......................... | B05B 9/06 239/162 |
| 4,313,726 A | 2/1982 | Chase | | |
| 4,357,670 A * | 11/1982 | McFarlane | .......... | A01M 7/0089 239/146 |
| 4,637,547 A * | 1/1987 | Hiniker | ................... | B05B 12/00 239/1 |
| 4,834,320 A * | 5/1989 | Tyson | ..................... | B64C 25/32 244/100 R |
| 4,937,754 A * | 6/1990 | Buisson | ................. | G01M 1/127 701/124 |
| 5,911,363 A * | 6/1999 | Oligschlaeger | ..... | A01M 7/0089 239/11 |
| 5,918,951 A | 7/1999 | Rudd, III | | |
| 6,175,370 B1 | 1/2001 | Kunimatsu | | |
| 6,684,147 B2 | 1/2004 | Park et al. | | |
| 7,035,725 B1 | 4/2006 | Park et al. | | |
| 7,735,186 B1 | 6/2010 | Vogel | | |
| 8,332,114 B2 | 12/2012 | Whittingham | | |
| 8,412,434 B2 | 4/2013 | Rado | | |
| 2001/0019090 A1 | 9/2001 | Horev | | |
| 2002/0014259 A1 | 2/2002 | Hahul | | |
| 2005/0051666 A1* | 3/2005 | Lee | ......................... | B64C 30/00 244/10 |
| 2006/0113425 A1* | 6/2006 | Rader | ..................... | B64C 15/00 244/17.11 |
| 2007/0158449 A1 | 7/2007 | Hoffman et al. | | |
| 2008/0154471 A1 | 6/2008 | Garcia et al. | | |
| 2009/0088911 A1* | 4/2009 | Paillard | ................... | B64C 17/10 701/4 |
| 2010/0044515 A1* | 2/2010 | Neto | ..................... | G01M 1/127 244/135 C |
| 2010/0070115 A1 | 3/2010 | Villaume | | |
| 2011/0046820 A1* | 2/2011 | Lohmann | ............ | G01F 23/0076 701/3 |
| 2013/0126677 A1 | 5/2013 | Mark et al. | | |

OTHER PUBLICATIONS

Federal Aviation Administration, Aircraft Weight and Balance Handbook FAA-H-8083-1A, 2007.*
Milton Abramowitz and Irene A. Stegun, National Bureau of Standards Applied Mathematics Series: Handbook of Mathematical Functions with Formulas, Graphs, and Mathematical Tables, 1972.*

* cited by examiner

ON-BOARD WATER SPRAY SYSTEM FOR AIRCRAFT

CROSS-REFERENCE TO RELATED APPLICATIONS

This application claims priority to U.S. patent application Ser. No. 12/760,939, filed Apr. 15, 2010, the disclosure of which is incorporated herein in its entirety by reference.

BACKGROUND OF THE INVENTION

1. Field of the Invention

The invention relates generally to the field of simulating wet surfaces for testing. More specifically, the invention relates to the field of testing the performance of aircraft tires and/or braking systems on wet runways.

2. Description of the Related Art

Conventionally, aircraft braking systems are subject to tests to see how they will perform on wet runways by manually dousing the runway surfaces with water and then landing the plane.

Testing systems have been developed to simulate these conditions. For example, in one system water is distributed onto the runway using a gravity fed tank on a trailer that is being pulled by a motor vehicle. Water is then dropped onto the ground in front of a test wheel which is also located on the trailer.

SUMMARY

Embodiments of the present invention include a system for simulating wet runway conditions. The system, in one embodiment, includes a liquid container situated on an aircraft. A liquid conduit fluidly connects the liquid container to a nozzle that is positioned to spray a liquid onto the ground in front of a wheel of the aircraft. In some embodiments a fan-shaped nozzle is used to produce a spray which creates a substantially uniform application of the liquid on the ground surface. In some embodiments, the fan-shaped spray pattern creates a depth of application that is around 0.04 inches of water.

The container can be a tank system which receives air under pressure from an air source, e.g., bleed air, to compel the delivery of water from the tank to the nozzle. The tank can include a relief valve to avoid over pressurization.

In embodiments, the system can include a liquid flow control system. This system controls the flow of water to the nozzle. It comprises a flow control valve for conditionally metering the amount of flow in the liquid conduit to establish a desirable flow rate of the liquid to the nozzle. This enables the flow control needed, but in yet other embodiments the system can include a controller, e.g., microcomputer. In one respect, the controller can receive on off signals from a switch in the cockpit to turn the spray system on and off.

Once on, some embodiments of the system include a speed sensor and a flow rate meter. The controller receives signals from the speed sensor and flow meter. This enables the system to establish a flow rate that establishes a substantially consistent application depth on the runway that accommodates speed changes. The flow control valve meters using the speed and flow data received to establish a flow rate that is appropriate at the given speed.

In another embodiment, an aircraft system comprises two tanks. A first liquid tank is located on a first side of an initial center of gravity of the aircraft, e.g., in front of the aircraft. The second liquid tank is located on an opposite side of the initial center of gravity for the aircraft, e.g., in back. The center of gravity can be adjusted in flight using a fluid control system that allows for changes in the tank fill levels to effect the change in center of gravity for the aircraft. This dual-tank embodiment can be used in cooperation with a spray system like that discussed above. To do so, one or both of the dual tanks would be fluidly connected to at least one nozzle used to spray a liquid onto a ground surface in front of a wheel of the aircraft to create a simulation of a wet runway.

Also disclosed is an embodiment that is a method for testing aircraft performance. This method involves putting a liquid container on an aircraft; filling the container with a liquid; using air pressure to compel the liquid; regulating flow of the liquid using a flow controlling valve; and applying the flow of liquid to a ground surface in front of a wheel of the aircraft in a substantially uniform manner when the aircraft is moving on the ground surface. This method, in embodiments enables automatically controlling a speed of the flow of the liquid using ground speed and flow rate data and then increasing the openness of the flow control valve if the flow rate value is below an acceptable deviation from an ideal flow rate at the speed; and decreasing the openness of the flow controlling valve if the flow rate value is above an acceptable deviation from the ideal flow rate at the speed. In some embodiments, the automatic control processes are executed in a loop so that the openness of the flow control valve is continually maintained inside acceptable ranges in consideration of ground speed.

BRIEF DESCRIPTION OF THE SEVERAL VIEWS OF THE DRAWINGS

Illustrative embodiments of the present invention are described in detail below with reference to the attached drawing figures, which are incorporated by reference herein and wherein.

DETAILED DESCRIPTION

Figure 1:
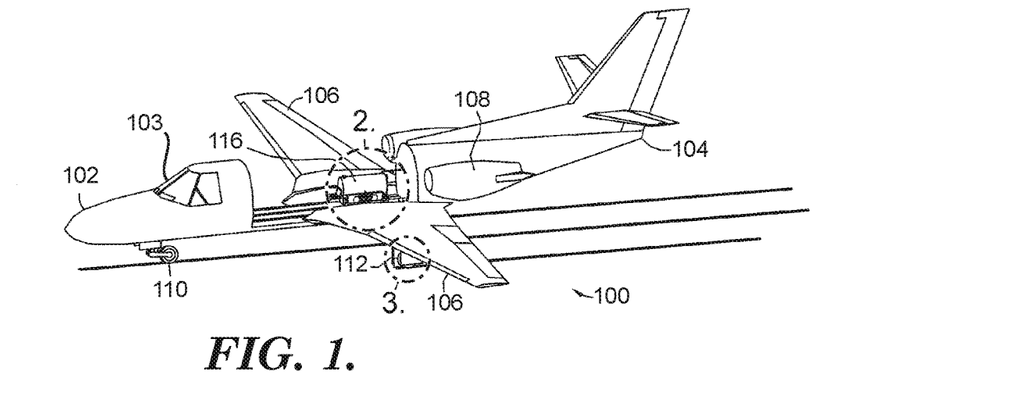
FIG. 1 is a perspective view of an aircraft including the on-board spray systems in one embodiment.

Embodiments of the present invention provide, in part, a system for simulating wet runway conditions. Wet conditions on runways are traditionally simulated using ground vehicles that apply water onto the runway. The present invention provides an independent method to simulate wet runways by using a system that does not require ground vehicles, but can utilize an aircraft 100. FIG. 1 shows the aircraft 100. As is typical, the aircraft has a nose 102, a cockpit 103, tail 104, wings 106, engines 108, a nose wheel 110, and rear wheels/tires 112.

Figure 2:
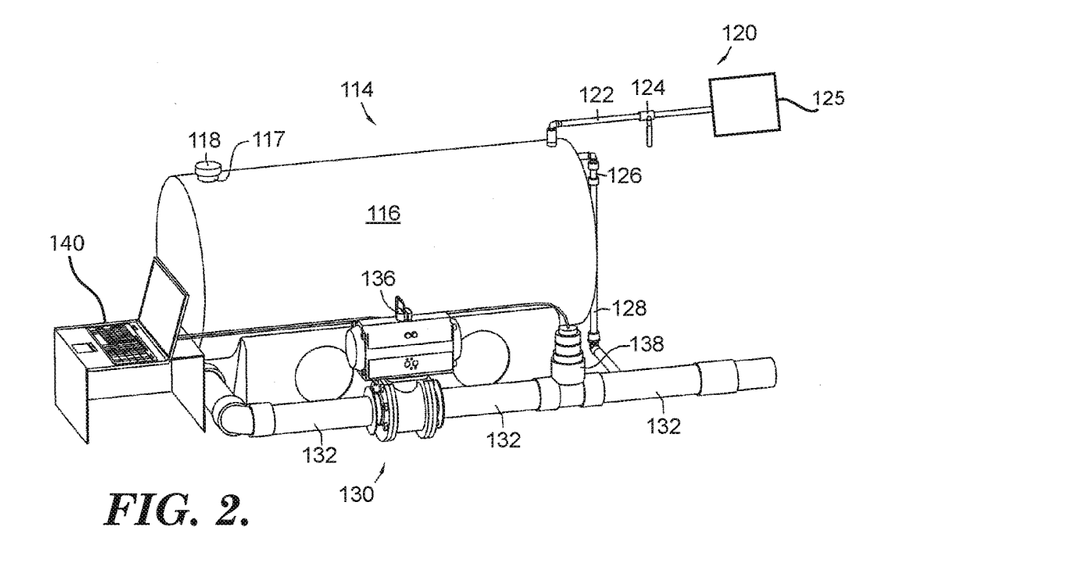
FIG. 2 is a detailed view 2 taken from FIG. 1 showing the liquid supply and flow control components in embodiments.

FIG. 2 shows an on-board water spray system 114 which may be included on the aircraft 100 for testing. The system contains a liquid tank 116. This liquid tank 116 is situated in the aircraft 100. The liquid tank 116 is filled with a liquid, e.g., water, through an opening 117. The opening 117 is closed with a cap 118. The cap 118 is removed when water is being filled into the tank. After the liquid tank 116 is filled up to the desired level, the cap 118 is placed back on the opening 117 to close the opening. The cap 118, when reattached, ensures that no water spills out of the tank when the tank is filled with water. The tank 116 is normally not fully filled with water to ensure that the bleed air can enter into the tank and pressurize the water in the tank effectively, as will be discussed later. The cap 118 is generally placed in position to close the opening 117 even when the system 114 is not in operation, to ensure that unintended objects do not get into the liquid tank 116.

The on-board water spray system may include a tank pressurization system 120. The tank pressurization system 120 is used to control the pressure at which the water inside the tank is stored. The liquid tank 116 is connected to one end of a conduit 122. The other end of conduit 122 is connected to a pressure source 125 which is used to keep the pressure in the liquid tank 116 at a desired level. In one embodiment, bleed air, which is compressed air taken from the engine 108, may be utilized as the source that provides the pressurized air to the liquid tank 116. Alternatively, the water could be mechanically driven by, e.g., a pump system (not shown). An air pressurized tank, however, has been used here in order to avoid limitations existing with mechanical solutions, e.g., lack of flow rate generation capabilities.

The conduit 122 may contain a manual shutoff valve 124, which is used to manually open the tank up to pressurization for testing, or to close off the flow of pressurized air into the liquid tank 116 when the tank does not need to be pressurized, e.g., before or after testing.

As is known by those skilled in the art, regulated bleed air sources are available in most turbine powered aircraft which can be tapped into to supply the required bleed air to conduit 122. Normally the air is available/regulated to approximately 20 psi. This value may, of course, vary considerably depending on the sort of aircraft involved. But generally speaking, most turbine aircraft have some available bleed air arrangement that can be used to pressurize a water tank. In the preferred embodiment, a 20 psi pressure is used. It is likely, however, that the air pressure used will be ramped down from this level to accommodate different system configurations.

The tank 116, in the FIG. 2 embodiment, includes a relief valve 126 and a drain line 128. Relief valve 126 is selected such that it prevents over pressurization in the tank. As discussed above, the pressurized air is at about 20 psi. Thus, tank 116 is adapted to accommodate this elevated pressure. But in case the pressure in the tank somehow reaches unacceptable levels, the relief valve will open up as a precaution. Some excess water may also drain out of the drain line 128 along with the bleed air. Thus, drain line 128 directs the water outside the aircraft.

Figure 3:
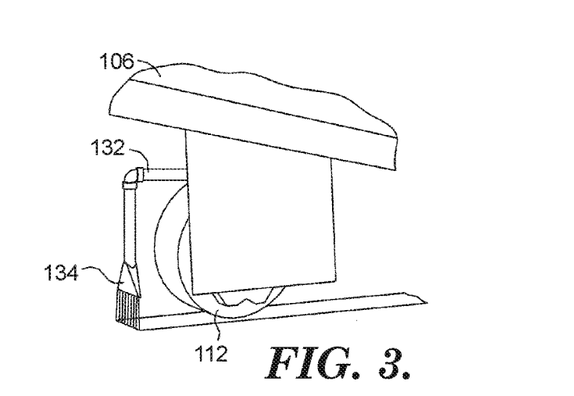
FIG. 3 is detail 3 taken from FIG. 1 showing the nozzle assembly in one embodiment.

The on-board water spray system 114 includes a flow control system 130. Flow control system 130 includes a flow conduit 132. Flow conduit 132 is connected to the liquid tank 116 at a first end, and to a nozzle 134 at a second end. As shown in FIG. 3, the nozzle 134 is placed in front of each of the rear wheels 112 of the aircraft 100. Looking at FIG. 2, it can be seen that only one conduit 132 is shown. But in the preferred embodiment, a substantially symmetrical arrangement on the opposite side of the aircraft would be used to supply identical water spray to the rear wheel on the other side of the aircraft. This could be done using a Y-branching junction to break the water supply in two and supply the nozzle on the opposite side of the aircraft. It should also be noted that for aircraft having two rear wheels on each side, a total of four nozzles and supporting conduit arrangements would be needed.

Similarly, it is contemplated that an additional spray nozzle can similarly be placed in front of the nose wheel 110 of the aircraft to test for steering authority. This forward nozzle could be supplied from a conduit branched from the already-depicted tank, or alternatively from a separate tank arrangement. Thus, although the embodiment shown in FIGS. 1-4 depict only one nozzle, it will be desirable in many instances to use dual nozzles that spray in front of both rear wheels.

Figure 1A:
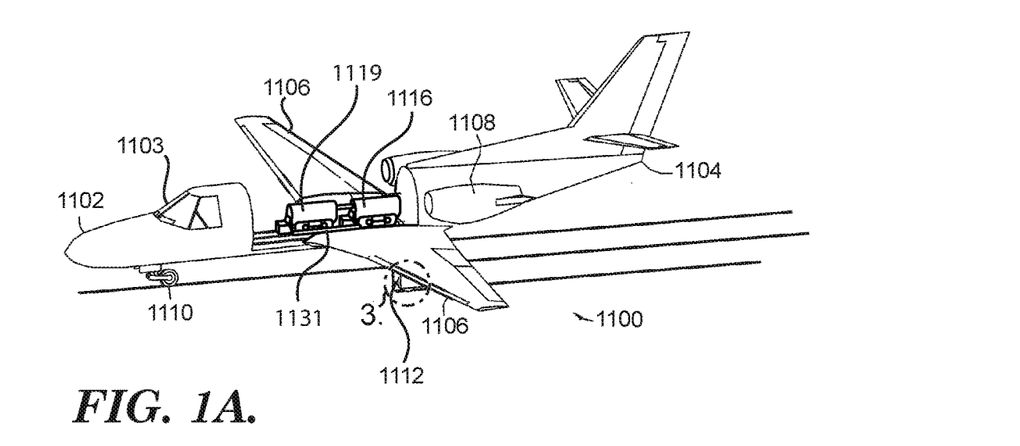
FIG. 1A is a perspective view of an aircraft including an on-board center of gravity manipulation system in one embodiment of the present invention.

It should be noted that, in yet another embodiment, dual tanks 1116 and 1119 (one forward, and one aft) could be used to create a center-of-gravity (CG) manipulation system. FIG. 1A shows the aircraft 1100. As is typical, the aircraft has a nose 1102, a cockpit 1103, tail 1104, wings 1106, engines 1108, a nose wheel 1110, and rear wheels/tires 1112. The aircraft system comprises two tanks 1116 and 1119. A first liquid tank 1116 is located on a first side 1121 of an initial center of gravity CG of the aircraft 1100, e.g., in front of the aircraft. The second liquid tank 1119 is located on an opposite side 1123 of the initial center of gravity CG for the aircraft 1100, e.g., in back. The center of gravity CG can be adjusted in flight using a fluid control system 1131 that allows for changes in each tank fill levels to effect the change in center of gravity CG for the aircraft 1100. Oftentimes, it is desirable in aircraft testing to observe aircraft performance under a range of CG locations to define a safe CG range. In order to accomplish this, the front and rear tanks could be selectively filled to different relative values to thus, change CG in flight. Starting with partially filled front and back tanks, and then using an inter-tank pumping capability to transfer water from the front tank to the back, or vice versa to accomplish a CG shift.

This dual-tank embodiment can be used in cooperation with a spray system 114 like that discussed above. To do so, one or both of the dual first and second tanks 1116 and 1119 would be fluidly connected to at least one nozzle used to spray a liquid onto a ground surface 1127 in front of a wheel 1110 or 1112 of the aircraft 1100 to create a simulation of a wet runway.

As shown in FIG. 2, the on-board water spray system may include a flow control system 130 that is designed to manage the quantity of water that is sprayed out of the nozzle 134. The flow of water being sprayed out of the nozzle is controlled by a control valve 136. The control valve 136 may be a servo-controlled valve, or some other known equivalent. This control valve 136 can be opened, closed, or put in intermediate positions to establish a desirable rate of flow of the water from the tank 116 to the nozzle 134. The flow control system includes a flow meter 138. The flow meter 138 quantifies the amount of liquid that is flowing out of the nozzle 134 at a given time.

Figure 4:
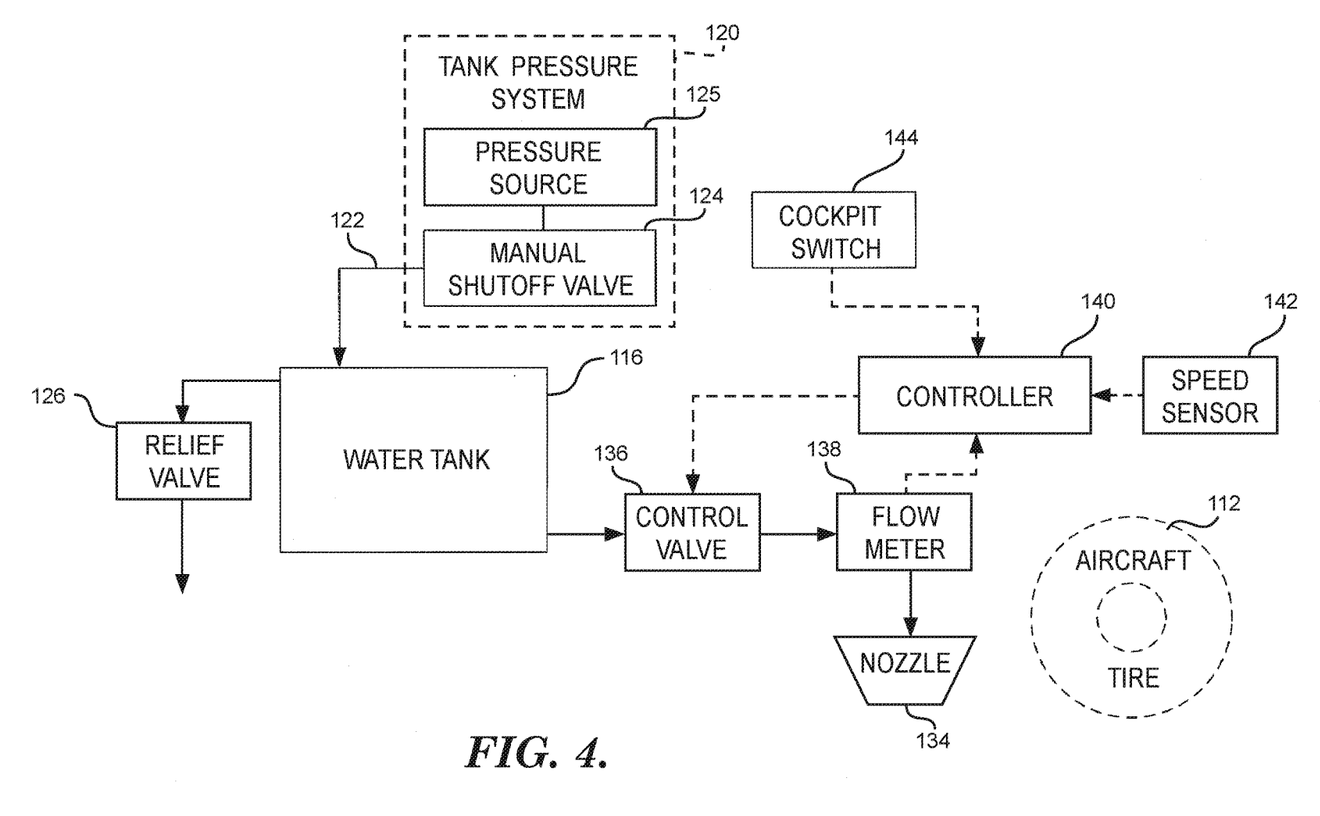
FIG. 4 is a schematic showing the interrelation of the many components in embodiments.

As shown in FIG. 4, the flow control system 130 includes a controller 140. Controller 140 could be one of numerous known smart devices, e.g., a personal computer, a programmable logic controller, microcomputing device, or a single board device. The controller 140 is electrically connected to the control valve 136, the flow meter 138, and a speed sensor 142 in a known manner. The speed sensor 142 may consist of a global positioning system, or derive readings from an electro-mechanical wheel speed detector arrangement commonly used with anti-skid systems. Regardless of particular configuration, the speed sensor 142 measures the ground speed of the aircraft 100.

The controller 140 is also connected to a cockpit switch 144. The cockpit switch 144 is situated in the cockpit 103. The cockpit switch 144 enables a user to start and stop the flow control system 130 from the cockpit of the aircraft 100 while maneuvering the aircraft 100 by sending a signal to the controller using known technologies.

Figure 5:
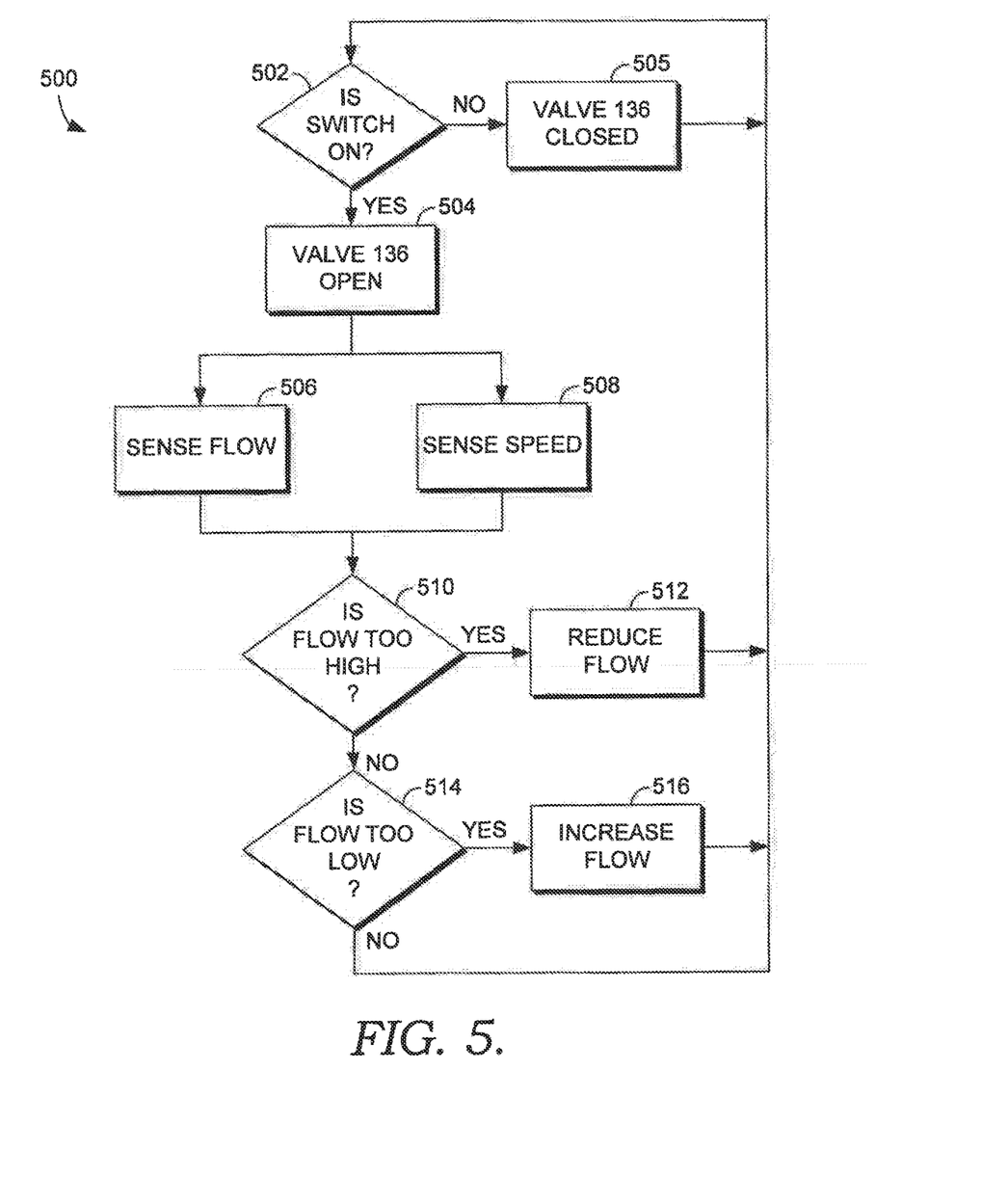
FIG. 5 is a flow diagram showing the processes running on the system controller in embodiments.

FIG. 5 is a flow chart including steps that outline the processes running on controller 140. In a first step 502, an inquiry is made as to whether the switch 144 in the cockpit is on. So long as switch 144 is off, the flow control valve 136 will remain closed in a step 505 and the process will loop between steps 505 and 502 indefinitely until the system is switched on. Once switch 144 is flipped to on, the controller (in step 502) recognizes this and valve 136 is opened up in a step 504. Initially, in step 504, the valve 136 will be opened to a starting point that is estimated to provide a starting flow rate. The controller then receives this flow rate from flow meter 138 and also the sensed speed from speed sensor 142 in steps 506 and 508, respectively.

Once this information has been received by the controller 140, the process moves on to a query step 510 in which a determination is made as to whether the flow rate is too high considering the speed sensed from the speed sensor 142. The controller 140 compares the inputs from the flow meter 138 and the speed sensor 142 with a pre-set look up table.

Figure 6:
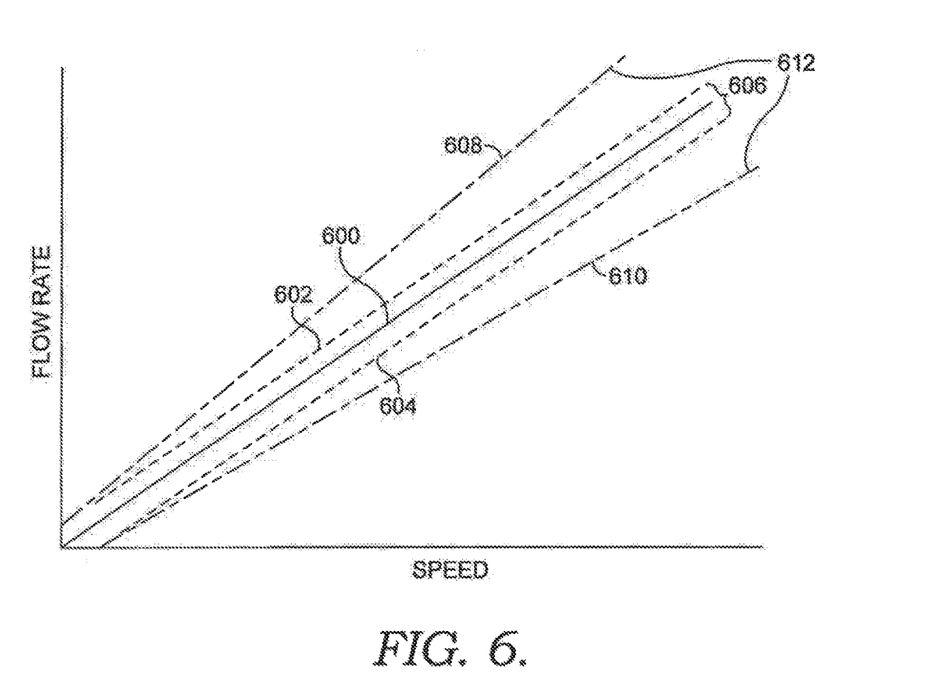
FIG. 6 is a chart which reflects how the deadband ranges are created for the lookup tables used in an embodiment of the invention.

Referring to FIG. 6, a graphical representation of the data included in the look up table can be seen. Referring to the figure, a line 600 is a linear plot of the ideal flow rates at each speed sensed for the aircraft to maintain the water deposited on the runway at a desired depth, e.g., 0.04 inches in one embodiment. In one embodiment, a constant dead band range 606, e.g., plus or minus 0.5 gpm in some embodiments, is created about ideal line 600 between maximum 602 and minimum 604. Lines 602 and 604, in this embodiment, are parallel with, and equidistant from ideal line 600. The displacement of each of lines 602 and 604 from line 600 represents a predetermined acceptable deviation from the ideal. If the sensed flow rate value at the sensed speed exceeds the upper boundary line 602, then the answer to query step 510 will be yes, and the flow will be reduced in a step 512. More specifically, the controller 140 sends a signal to the flow control valve 136 causing it to close slightly. Once the flow control valve has thus been closed to an extent in step 512, the process loops back up and is reintroduced to step 502.

If the sensed flow rate at the given speed falls below upper boundary line 602, then the process moves on to a query step 514 where a determination is made as to whether the flow rate is too low. In this step, if the sensed flow rate at the sensed speed falls below the values at predetermined lower boundary line 604, then the answer in step 514 will be yes, and the process will move on to a step 516 in which the controller will send a signal to flow control valve 136 opening it up slightly, and the process will then loop back up to step 502.

If, however, in step 514 the flow rate value at the sensed speed is above line 604, then the process immediately loops back up and is reintroduced to step 502 without executing step 516.

It can be seen that the continuous looping process in flow 500 will result in the continuous incremental adjustment in the openness of flow control valve 136 when the system is active.

In an alternative embodiment, a maximum line 608 and a minimum line 610 together create an increasingly expanding range 612 about ideal line 600. This embodiment will result in the acceptable deviation for flow rate being greater at higher ground speeds detected.

In terms of the signaling, the output of the controller 140 being received by the control valve 136 may be a DC voltage signal ranging from zero to 10 volts. An output of zero volts from the controller may close the control valve 136 completely, an output of 10 volts may open the control valve 136 fully, and the intermediate values may open the control valve 136 to varying degrees to establish the desired amount of flow from the nozzle 134. In this case, the flow reductions made in step 512 will be made incrementally with each loop, as will the flow increases of step 516 with each execution.

These FIG. 5 processes of the controller acting in cooperation with the speed sensor 142, flow meter 138, and flow control valve 136 enable the current flow of water from the nozzle 134 to be regulated so that a nearly uniform layer of water is deposited onto the ground in front of the wheel 112. A depth of 0.04 inches of water is considered to be generally representative of wet runway conditions. Thus, in a preferred embodiment, the dead band ranges (e.g., ranges 606 and 612) are selected such that they result in a consistent, nearly uniform, layer of water that is 0.04 inches deep regardless of the current, and/or changing ground speeds of the aircraft. Thus, when the ground speed of the aircraft 100 increases, the controller 140 opens valve 136 to further increase the flow of water out of the nozzle 134. When the speed of the aircraft decreases, the controller 140 closes valve 136 further. In this manner varying speeds are accommodated.

When the pilot (or another) moves switch 144 to "off" position, this will be recognized in looping step 502, and the valve 136 is closed in a step 505. The process will remain in a mode looping between steps 502 and 505 until the switch is flipped back on.

Systems of the aircraft 100 can now be tested in wet runway conditions. For example, the performance of the braking system of an aircraft 100 may be evaluated in the simulated wet runway conditions. Similarly, the performance of the tires of the aircraft 100 may be tested in these simulated wet runway conditions.

After a testing run has been completed, the tank is able to be refilled. The switch will be off, and flow control valve 136, thus, will be closed. Additionally, the user will close off the tank from the bleed air using valve 124. Then, the user can remove the pressure releasing safety cap 118, and fill the tank 116 with water.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and sub combinations are of utility and may be employed without reference to other features and sub combinations and are contemplated within the scope of the claims. Not all steps listed in the various figures need be carried out in the specific order described.

The invention claimed is:

1. A system for simulating wet runway conditions, comprising:
   a first liquid tank situated on an aircraft;
   a pressure source; and
   a pressure conduit for providing pressure to the first liquid tank from the pressure source; and
   a spray nozzle positioned in front of a wheel of the aircraft, and pressurized liquid from the first liquid tank flowing through the spray nozzle;
   a control valve establishing a rate of flow of the pressurized liquid;
   a pressure control subassembly in connection with the pressure source and pressure conduit, the pressure control subassembly preventing over-pressurization in the first liquid tank by releasing pressure when a predetermined amount of pressure is met;
   a flow meter quantifying the rate of flow of the pressurized liquid;
   a speed sensor measuring speed of the aircraft;
   a controller connected to the control valve, the flow meter, and the speed sensor, and able to receive liquid flow information from the flow meter and speed of the aircraft from the speed sensor;
   wherein the controller causes liquid to be sprayed onto the runway at an actual flow rate; the actual flow rate being within an acceptable range of deviation of an ideal flow rate; the ideal flow rate being proportional to the aircraft speed; the acceptable range of deviation increasing with increasing aircraft speed; and
   an inter-tank fluid redistribution arrangement associated with the first liquid tank, the arrangement configured to enable the observation of aircraft performance under a range of varied center-of-gravity locations by pumping liquid to forward or backward locations on the aircraft.

2. The system of claim 1, wherein the controller is in electronic communication with the control valve, the flow meter and the speed sensor.

3. The system of claim 2, wherein the controller is further in electronic communication with a switch in a cockpit of the aircraft.

4. The system of claim 2, wherein the controller is selected from the group consisting of: a personal computer, a programmable logic controller, a microcomputing device, and a single board device.

5. The system of claim 4, wherein the spray nozzle is one of a plurality of spray nozzles, each spray nozzle being positioned in front of the wheel of the aircraft.

6. The system of claim 1, wherein the spray nozzle emits the pressurized liquid in a substantially fan-shaped spray pattern.

7. The system of claim 1, wherein a fluid control system transfers pressurized liquid from the first liquid tank to a second liquid tank and the second liquid tank to the first liquid tank to shift the initial center of gravity beyond a safe range of the center of gravity.

8. A system on an aircraft for simulating wet runway conditions, comprising:
   a first liquid tank containing liquid, the first liquid tank being forwardly located relative to the an initial center of gravity of the aircraft;
   a second liquid tank containing liquid, the second liquid tank being rearwardly located relative to the initial center of gravity of the aircraft;
   a regulated source of pressurized air pressurizing the liquid to pressurized liquid in the first and second liquid tanks;
   a pressure control subassembly in connection with the first and second liquid tanks, the pressure control subassembly preventing over-pressurization in the first and second liquid tanks by releasing pressure when a predetermined amount of pressure is met; and
   a fluid control system located on the aircraft, comprising:
      a control valve establishing a rate of flow of the pressurized liquid;
      a flow meter quantifying the rate of flow of the pressurized liquid;
      a speed sensor measuring the speed of the aircraft; and
      a controller connected to the control valve, the flow meter, and the speed sensor;
   wherein the controller causes liquid from each of the first and the second liquid tanks to be sprayed onto a ground surface in front of an aircraft wheel; an actual flow rate of the liquid being sprayed on the ground surface at a particular aircraft speed being within an acceptable range of deviation from the ideal flow rate;
   wherein the acceptable range of deviation of the actual flow rate from the ideal flow rate increases with increasing aircraft speed; and
   an inter-tank fluid redistribution arrangement enabling liquid to be pumped forward to the first tank or backward to the second tank, the arrangement configured to enable the observation of aircraft performance under a range of varied center-of-gravity locations for the purpose of defining a safe range for center of gravity.

9. The system of claim 8, wherein the controller is in communication with a switch in a cockpit of the aircraft, the switch operating between an on position and an off position.

10. The system of claim 9, wherein the controller is selected from the group consisting of: a personal computer, a programmable logic controller, a microcomputing device, and a single board device.

11. A method for testing performance of an aircraft comprising steps:
   a) providing a liquid spray system, comprising:
      a first liquid tank situated on a proximal side of an initial center of gravity of the aircraft;
      a second liquid tank situated on a distal side of the initial center of gravity of the aircraft such that the second liquid tank is both closer to a back of the aircraft and further away from a cockpit of the aircraft as compared to the first liquid tank; the second liquid tank being fluidly coupled to the first tank;
      a regulated source of pressurized air to pressurized liquid in the first and second liquid tanks;
      a first spray nozzle and a second spray nozzle, each being fluidly coupled to at least one of the first liquid tank and the second liquid tank; the first spray nozzle and the second spray nozzle respectively configured to spray pressurized liquid in front of a left wheel and a right wheel of the aircraft;
      a flow meter;
      a speed sensor for determining a speed of the aircraft;
      a controller in communication with the flow meter, the speed sensor, and the first and second liquid tanks;
   b) providing a speed of the aircraft to the controller;
   c) causing a center of gravity of the aircraft to shift outside a safe range of the center of gravity while the aircraft is airborne by using the controller to cause liquid to be pumped from the first liquid tank into the second liquid tank and by using the controller to cause liquid to be pumped from the second liquid tank into the first liquid tank, so as to test the performance of the aircraft under a range of the center of gravity to define the safe range of the center of gravity;

d) providing a look up table tabulating an ideal flow rate at which liquid is to be deposited onto a ground surface; the ideal flow rate being proportional to a speed of the aircraft; and e) using the controller to cause liquid from each of the first and the second liquid tanks to be sprayed onto the ground surface in front of the left and the right wheels; an actual flow rate of the liquid being sprayed on the ground surface at a particular aircraft speed being within an acceptable range of deviation from the ideal flow rate;

wherein the acceptable range of deviation of the actual flow rate from the ideal flow rate increases with increasing aircraft speed.

12. The system of claim 11, wherein the first and the second spray nozzles emit the pressurized liquid in a substantially fan-shaped spray pattern.

13. A method for testing performance of an aircraft comprising steps:

a) providing a liquid spray system, comprising:

a first liquid tank situated on a proximal side of an initial center of gravity of the aircraft;

a second liquid tank situated on a distal side of the initial center of gravity of the aircraft such that the second liquid tank is both closer to a back of the aircraft and further away from a cockpit of the aircraft as compared to the first liquid tank;

a spray nozzle; the spray nozzle being fluidly coupled to at least one of the first liquid tank and the second liquid tank;

a controller in communication with the first and second liquid tanks;

b) providing a speed of the aircraft to the controller;

c) causing a center of gravity of the aircraft to shift outside a safe range of the center of gravity while the aircraft is airborne by using the controller to cause liquid to be pumped from the first liquid tank into the second liquid tank, so as to test the performance of the aircraft under a range of the center of gravity to define the safe range of the center of gravity;

d) determining an ideal flow rate at which liquid is to be deposited onto a ground surface; the ideal flow rate being proportional to a speed of the aircraft; and e) using the controller to cause liquid from at least one of the first and the second liquid tanks to be sprayed onto the ground surface in front of a wheel of the aircraft; an actual flow rate of the liquid being sprayed on the ground surface at a particular aircraft speed being within an acceptable range of deviation from the ideal flow rate;

wherein the acceptable range of deviation of the actual flow rate from the ideal flow rate increases with increasing aircraft speed.

14. The method of claim 13, wherein the controller is a microcomputing device.

15. A method for testing performance of an aircraft comprising steps:

a) providing a liquid spray system, comprising:

a first liquid container situated forward relative to an initial center of gravity of the aircraft;

a second liquid container situated rearward relative to the initial center of gravity of the aircraft;

a spray nozzle; the spray nozzle being fluidly coupled to at least one of the first liquid container and the second liquid container;

a controller in communication with the first and second liquid containers;

b) providing a speed of the aircraft to the controller;

c) determining an ideal flow rate at which liquid is to be deposited onto a ground surface; the ideal flow rate being proportional to the speed of the aircraft; and d) using the controller to cause liquid from at least one of the first and the second liquid containers to be sprayed onto the ground surface in front of a wheel of the aircraft; an actual flow rate of the liquid being sprayed on the ground surface at a particular aircraft speed being within an acceptable range of deviation from the ideal flow rate;

wherein the acceptable range of deviation of the actual flow rate from the ideal flow rate increases with increasing aircraft speed;

e) providing a liquid manipulation system; and f) manipulating the center of gravity of the aircraft by using the liquid manipulation system to move liquid back and forth between the two containers to determine performance when the center of gravity is outside of normal ranges.

* * * * *